(12) United States Patent
Li et al.

(10) Patent No.: US 9,632,533 B2
(45) Date of Patent: Apr. 25, 2017

(54) STRETCHABLE WIRELESS DEVICE

(71) Applicant: VivaLnk Limited (Cayman Islands), Santa Clara, CA (US)

(72) Inventors: Jiang Li, Cupertino, CA (US); Junfeng Mei, Sunnyvale, CA (US)

(73) Assignee: VivaLnk, Inc., Santa Clara, CA (US)

( * ) Notice: Subject to any disclaimer, the term of this patent is extended or adjusted under 35 U.S.C. 154(b) by 214 days.

(21) Appl. No.: 14/511,578

(22) Filed: Oct. 10, 2014

(65) Prior Publication Data

US 2016/0028153 A1    Jan. 28, 2016

Related U.S. Application Data

(63) Continuation of application No. 14/491,665, filed on Sep. 19, 2014, now Pat. No. 9,513,666.

(60) Provisional application No. 62/029,334, filed on Jul. 25, 2014.

(51) Int. Cl.
| | |
|---|---|
| *H05K 7/00* | (2006.01) |
| *G06F 1/16* | (2006.01) |
| *A61M 35/00* | (2006.01) |
| *A61M 37/00* | (2006.01) |
| *H01Q 1/27* | (2006.01) |
| *H05K 1/02* | (2006.01) |
| *H05K 1/03* | (2006.01) |
| *H05K 1/14* | (2006.01) |
| *H05K 1/18* | (2006.01) |
| *H01Q 9/04* | (2006.01) |

(52) U.S. Cl.
CPC ............. *G06F 1/163* (2013.01); *A61M 35/00* (2013.01); *A61M 37/00* (2013.01); *H01Q 1/273* (2013.01); *H01Q 9/0407* (2013.01); *H05K 1/028* (2013.01); *H05K 1/0283* (2013.01); *H05K 1/0313* (2013.01); *H05K 1/142* (2013.01); *H05K 1/148* (2013.01); *H05K 1/183* (2013.01)

(58) Field of Classification Search
CPC ....... A61M 35/00; A61M 37/00; G06F 1/163; H01Q 1/273; H01Q 9/0407; H05K 1/028; H05K 1/0283; H05K 1/0313; H05K 1/142; H05K 1/148; H05K 1/183
See application file for complete search history.

(56) References Cited

U.S. PATENT DOCUMENTS

| | | | | |
|---|---|---|---|---|
| 5,749,365 A | * | 5/1998 | Magill | ................ A61B 5/0008 128/903 |
| 2004/0077189 A1 | * | 4/2004 | St. John | .................. H01R 4/04 439/60 |
| 2007/0270672 A1 | | 11/2007 | Hayter | |

(Continued)

*Primary Examiner* — Yuriy Semenenko
(74) *Attorney, Agent, or Firm* — SV Patent Service

(57) ABSTRACT

A wearable patch capable of wireless communications includes an adhesive layer, and a shearable circuit layer comprising a support substrate comprising one or more openings on the adhesive layer, wherein the one or more openings in the support substrate are so positioned to allow the shearable circuit layer to be sheared and elongated, and breathable. A conductive circuit is embedded in the support substrate. One or more semiconductor chips are in connection with the conductive circuit. An elastic layer is positioned on the shearable circuit layer. The one or more semiconductor chips and the conductive circuit can wirelessly communicate with an external device.

5 Claims, 13 Drawing Sheets

(56) References Cited

U.S. PATENT DOCUMENTS

| | | | |
|---|---|---|---|
| 2008/0247144 A1* | 10/2008 | Silverbrook | H01L 23/13 361/767 |
| 2009/0171180 A1 | 7/2009 | Pering | |
| 2010/0035539 A1* | 2/2010 | Yoshida | H01Q 1/2225 455/1 |
| 2011/0105952 A1* | 5/2011 | Bernstein | A61B 5/1411 600/573 |
| 2012/0242481 A1 | 9/2012 | Gernandt | |
| 2014/0061584 A1* | 3/2014 | Mahan | H01L 23/4334 257/13 |
| 2014/0104793 A1* | 4/2014 | Park | H05K 1/0283 361/749 |

* cited by examiner

STRETCHABLE WIRELESS DEVICE

BACKGROUND OF THE INVENTION

The present application relates to wearable wireless electronic devices, and in particular, to tag-like or patch-like wireless devices that can adhere to human skin.

Wearable patches or tags can communicate with smart phones and other devices using WiFi, Bluetooth, or NFC technologies. Near Field Communication (NFC) is a wireless communication standard which enables two devices in a short range to establish a communication channel within a short period of time through radio waves in the 13.56 MHz frequency range. NFC can be a useful technology for data transfer between two devices in close proximity to one another. Because it needs the two devices to be in close proximity to one another (less than 10 cm), it is more secure than other wireless technologies like Bluetooth and Wi-Fi. Hence, it can be seen as an easy and secure tool for establishing quick two-way connections for data transfer. NFC is a two-way communication tool, one of the devices/cards can have a passive NFC tag that can reduce the cost and still behave in the same way as any other RFID tag.

This communication standard is being increasingly adopted for use in wireless transactions, including money transfer, loyalty coupons, gift cards, transit passes, tickets, etc. Mobile handset manufacturing companies are increasingly integrating NFC hardware in their phones. For example, the 2014 CES badges employed NFC technology and have resulted in shorter lines, more badge functionality, and greater ease of use for attendees and exhibitors. NFC has also been increasingly used in the fields of medical devices, electronic health records, as well as wearable tagging devices.

Wearable tag (or patch) is an electronic tag that can be worn by a user. Wearable patch is required to directly stay on user's skin and function for an extended period of time from hours to months. A wearable patch can contain a micro-electronic system and can be accessed using NFC, Bluethooth, WiFi, or other wireless technologies. An authentication wearable tag can be used as a "password" similar to a barcode. For example, it can be used to recognize a user's smart phone for authentication purpose. It can also be integrated with different sensors for other purposes such as vital signs monitoring, motion track, skin temperature measurements and ECG detection.

Despite initial development efforts, conventional wearable devices still face several drawbacks: they may not provide adequate comfort for users to wear them; they may not stay attached to user's body for the required length of time; they are usually not aesthetically appealing.

Another drawback of conventional wearable patches is that the rigid polymer substrate does not allow much breathability to the skin. The build-up of sweat and moisture can cause discomfort and irritation to the skin, especially after wearing it for an extended period of time. In addition, their rigid substrates are very difficult to conform to curved surfaces.

Moreover, conventional wearable devices are often not robust enough to sustain repeated elongations during the movements of the body that the wearable patches are attached to. Under stress, different layers in wearable patches can break or delaminate rendering the patches inoperable.

There is therefore a need for more durable wearable patches that are also comfortable for users to wear.

SUMMARY OF THE INVENTION

The presently disclosure attempts to address the aforementioned limitations in conventional wearable patches. The disclosed wearable patches are highly compliant and flexible, while also being able to support the circuit, chips, and other electronic components in the wearable patch. The disclosed wearable patches can change their physical shape and dimension to relieve stresses such as repeated elongations, therefore increasing durability of the wearable patches as well as provide comfort to the user. The disclosed wearable patches can stay attached to skin for long period of time even enduring muscle movements underneath the skin to provide constant contact to the skin and comfort to the user.

The disclosed wearable patches are also breathable and comfortable for users to wear.

Furthermore, the disclosed wearable patches are aesthetically appealing.

In one general aspect, the present invention relates to a wearable patch capable of wireless communications, comprising: an adhesive layer; a shearable circuit layer that includes: a support substrate comprising one or more openings on the adhesive layer, wherein the one or more openings in the support substrate are so positioned to allow the shearable circuit layer to be sheared and elongated, and breathable; a conductive circuit embedded in the support substrate. The wearable patch includes one or more semiconductor chips in connection with the conductive circuit, and an elastic layer on the shearable circuit layer, wherein the one or more semiconductor chips and the conductive circuit can wirelessly communicate with an external device.

Implementations of the system may include one or more of the following. At least one of the openings can be surrounded by the conductive circuit in the support substrate. The conductive circuit can include an antenna circuit configured to receive or transmit wireless signals in communications with the external device. The elastic layer can include one or more recesses on a surface facing the shearable circuit layer, wherein the one or more recesses are configured to enclose the one or more semiconductor chips. The shearable circuit layer can include one or more sensors, actuators, or chemical delivery devices in connection with the conductive circuit. The shearable circuit layer can include one or more electronic components in connection with the conductive circuit, wherein the one or more electronic components are selected from the group consisting of capacitors, inductors, resistors, metal pads, diodes, transistors, and amplifiers. The support substrate can have a Young's Modulus higher than 0.5 Gpa. The support substrate can include polyimide, polyester, Aramid, glass epoxy, or polyethylene naphalate. The elastic layer can have a Young's Modulus lower than 0.3 Gpa. The elastic layer can include an elastomer material. The shearable circuit layer can include a graphic pattern, wherein the graphic pattern and the conductive circuit can be formed from a same layer of a conductive material. The one or more semiconductor chips and the conductive circuit can wirelessly communicate with the external device based on near field communication (NFC), Wi-Fi, Bluetooth, or RFID wireless communication standard.

In another general aspect, the present invention relates to a wearable patch capable of wireless communications which includes an adhesive layer and a multi-layer circuit structure, comprising: a support substrate layer comprising one or more openings on the adhesive layer, wherein the one or more openings in the support substrate layer are so positioned to allow the multi-layer circuit structure to be sheared and elongated, and breathable; a conductive circuit embedded in the support substrate layer; a strap layer disposed across one of the one or more openings; and one or more semiconductor chips on the strap layer. The wearable patch can also include an elastic layer on the multi-layer circuit structure. The one or more semiconductor chips are in electrical connection with the conductive circuit, wherein the one or more semiconductor chips and the conductive circuit are configured to wirelessly communicate with an external device.

These and other aspects, their implementations and other features are described in detail in the drawings, the description and the claims.

DETAILED DESCRIPTION OF THE INVENTION

Figure 1:
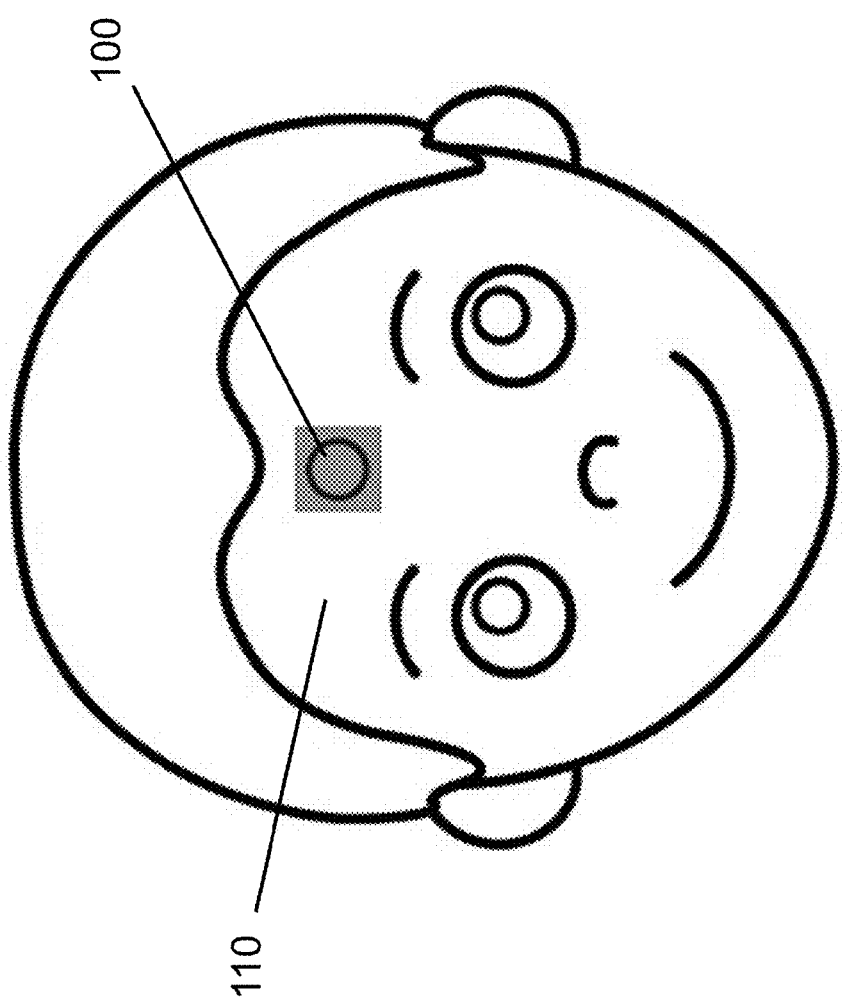
FIG. 1 illustrates the usage of a wearable patch that is attached to a user's skin.

Referring to FIG. 1, a wearable patch 100 can be placed on and adheres to a person's skin 110 on his or her body such as forehead, hand, wrist, arm, shoulder, waist, leg, foot, etc.

As discussed above, there are several challenges for wearable patches on human skin. The patches need to stay on skin for an extended period enduring various daily activities such as taking showers or bathes, swimming, exercises, holding weights, etc. The patches also need to change their physical dimension to adhere to the skin, which will change its shape by the muscle movements underneath. The patches are also rubbed by clothing numerous times a day. While it is very challenging to keep Band-Aid stickers to stay on skin for a week, conventional wearable patches normally have much stiffer rigid substrates, which make them more easily rubbed off than Band-Aid stickers. In addition, it is also very challenging to make a tag or a patch to be comfortable to the user. Ideally the patch needs to be stretchable, flexible, and breathable.

Figure 2:
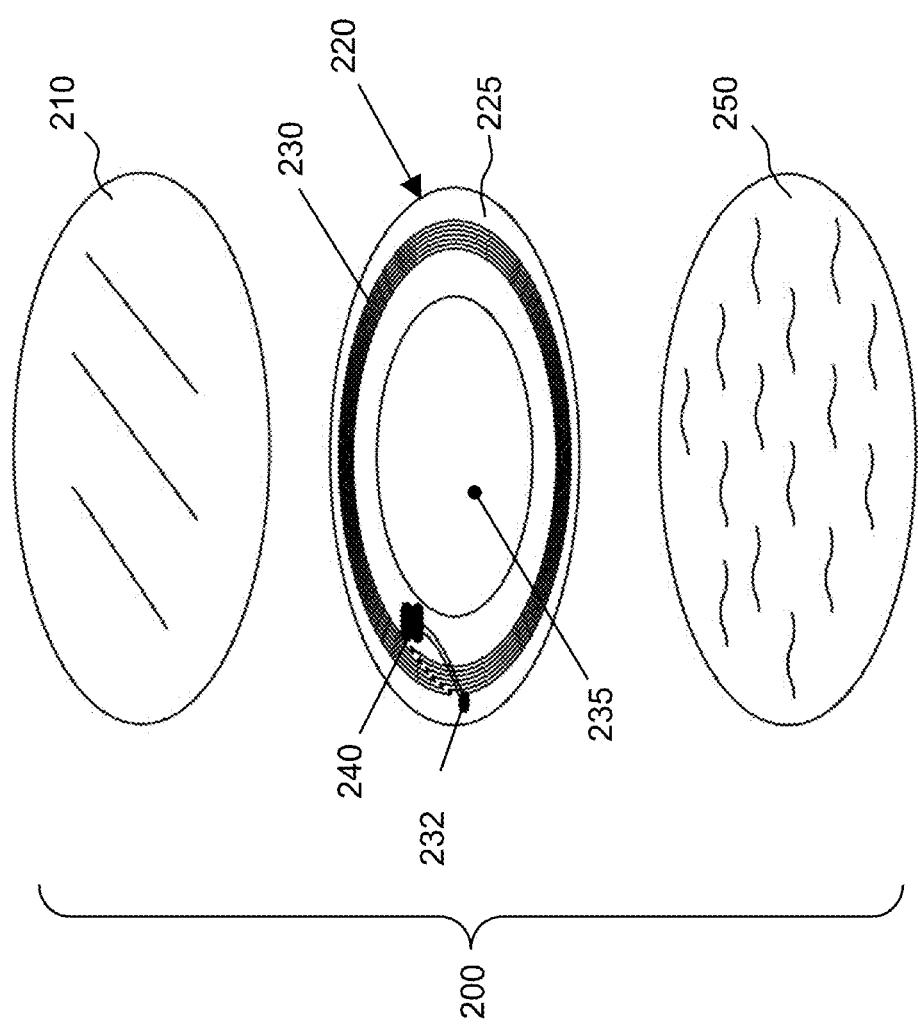
FIG. 2 is an exploded perspective view of an exemplified compliant multi-layer wearable patch in accordance with some embodiments of the present invention.

The presently disclosure aims to overcome the drawbacks in the conventional wearable patches, and to provide highly compliant, flexible, and durable wearable wireless patches that are also comfortable for users to wear. Referring to FIG. 2, a wearable patch 200 includes an elastic layer 210, a shearable circuit layer 220, and an adhesive layer 250. The shearable circuit layer 220 includes a non-conductive support substrate 225, an antenna circuit 230 embedded in the support substrate 225, a metal pad 232, and a semiconductor chip 240 electrically connected to the metal pad 232. The antenna circuit 230 is configured to receive or transmit wireless signals in communications with the external device.

The elastic layers 210 can be made of a viscoelastic polymeric material having low Young's modulus and high failure strain. In some embodiments, the elastic layer 210 has Young's Modulus <0.3 Gpa. In some cases, the elastic layer 210 and can have Young's Modulus <0.1 Gpa to provide enhanced flexibility and tackability. Materials suitable for the elastic layer 210 include elastomers, viscoelastic polymers, such as silicone, and medical grade polyurethane that is a transparent medical dressing used to cover and protect wounds with breathability and conformation to skin.

The support substrate 225, on the other hand, is rigid enough to provide support to the antenna circuit 230 and the semiconductor chip 240. In some embodiments, the support substrate 225 can have Young's Modulus larger than 0.5 Gpa, such as in a range between 1.0-10 Gpa. Examples of materials suitable for the substrate 225 include Polyimide, polyester, Aramid, Composite, Glass epoxy, and Polyethylene naphalate. Importantly, the support substrate 225 is structured to provide stretchability to the shearable circuit layer 220. The support substrate 225 includes an opening 235 in the center of the antenna circuit 230, which makes the shearable circuit layer 220 shearable and stretchable when the wearable patch 200 is stretched or elongated. By strategically forming openings in the support substrate 225, the effective elasticity of the support substrate 225 is increased significantly above the intrinsic elasticity the material in the support substrate 225 (the effective elastic constant is decreased). In some embodiments, the support substrate 225 is thinner than 0.2 mm to allow flexibility (bendability), and high effective elasticity of the support substrate 225 is strategically structured by openings. In some embodiments, the support substrate 225 is thicker than 0.001 mm to allow enough strength to support the circuits and chips during manufacturing process. Inside the substrate 225, it can have 0 to 20 layers of conductive metals to provide additional wiring capabilities. It may also embed electronic components such as passives, semiconductor chips, inside of the support substrate.

Thus, the elastic layers 210 and the shearable circuit layer 220 provide support as well as compliance, stretchability, flexibility, breathability, and durability to the wearable patch 200. The elastic layers 210 and the shearable circuit layer 220 are compliant and can conform to the skin under different moving positions, which can repeatedly elongate and compress the wearable patch 200. The elastic layers 210 and the shearable circuit layer 220 are also breathable to allow aspiration and moisture from the skin to be released to the environment. The opening 235 in the middle of the shearable circuit layer 220 provides additional breathability to the wearable patch 200.

In some embodiments, the antenna circuit 230 and the semiconductor chip 240 are configured to communicate with external devices based on NFC standard, RFID, Wi-Fi, Bluetooth, or other types of wireless communication standard. Examples of external devices include smart phones, computers, mobile payment devices, scanners and readers (e.g. RFID readers), medical devices, security systems, personal identification systems, etc.

The antenna circuit 230 can be compatible for NFC communications in a frequency range near 13.56 MHz, as described above, as well as UHF RFID at about 915 MHz, Bluetooth in 2.4 GHz or 5 GHz frequency ranges, and other types of wireless communications.

Figure 3:
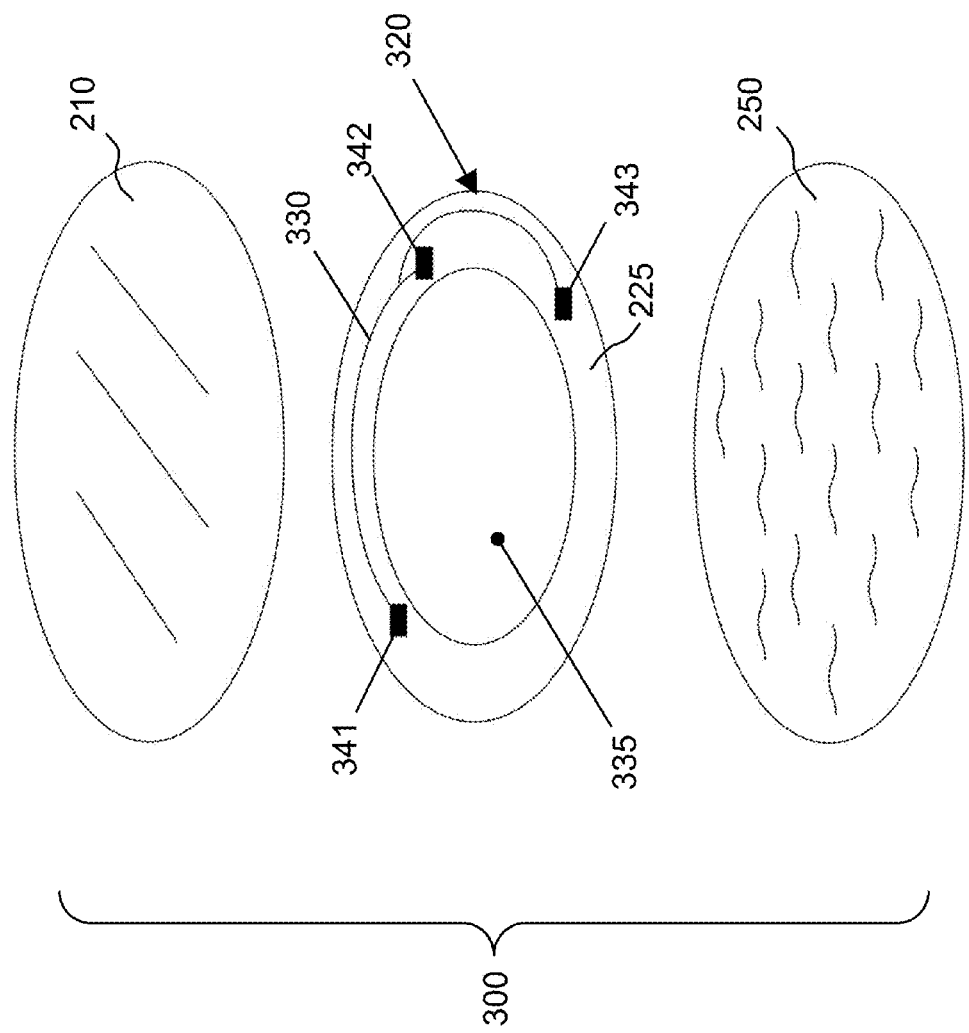
FIG. 3 is an exploded perspective view of another exemplified compliant multi-layer wearable patch in accordance with some embodiments of the present invention.

In some embodiments, referring to FIG. 3, a wearable patch 300 includes an elastic layer 210, a shearable circuit layer 320, and an adhesive layer 250. The shearable circuit layer 320 includes a support substrate 225 that includes an opening 335 in the middle, a conductive circuit 330, and semiconductor chips 341-343 that are electrically connected to the conductive circuit 330. The semiconductor chips 341-343 can perform communications, logic, signal or data processing, control, calibration, status report, diagnostics, and other functions. The semiconductor chips 341-343 can include sensors, actuators, and chemical delivery devices.

The elastic layer 210 is breathable to allow aspiration and moisture from the skin to be released to the environment. The opening 335 provides additional breathability to the wearable patch 300. Small opening holes can also be made on substrate 225 to enhance the breathability as well as the effective elasticity of the substrate.

An advantage of the disclosed wearable patch is its mechanical robustness comparing with conventional wearable patches. The latter has high rigidity and sometimes easy to fracture or delaminate. The shearable circuit layer is structured to be shearable and compliant; the elastic layer 210 is made of materials such as a polymer material such as an elastomer, which together makes the wearable patches highly compliant, stretchable, and flexible. The elastic layer 210 and the support substrate 225 can reduce the impact of rubbing force on the rigid dry inlay layer underneath, which provides better protection to the semiconductor chip 240 and the antenna circuit 230. The wearable patches are thus resilient to starching and compressing during wearer's body movement. Thus, the elastic layers 210 and the support substrate 225 can reduce the probability of falling off, thus increasing the life span of the wearable patch.

The adhesive layer 250 can be pressure sensitive, which allows the wearable patches 200, 300 tightly adhere to human skin under pressure, applied for example by a thumb. For instance, the adhesive layer 250 can be made of a medical pressure sensitive adhesive. An example of such adhesive is medical grade tackified Hypoallergenic Pressure Sensitive Adhesive.

Figure 4:
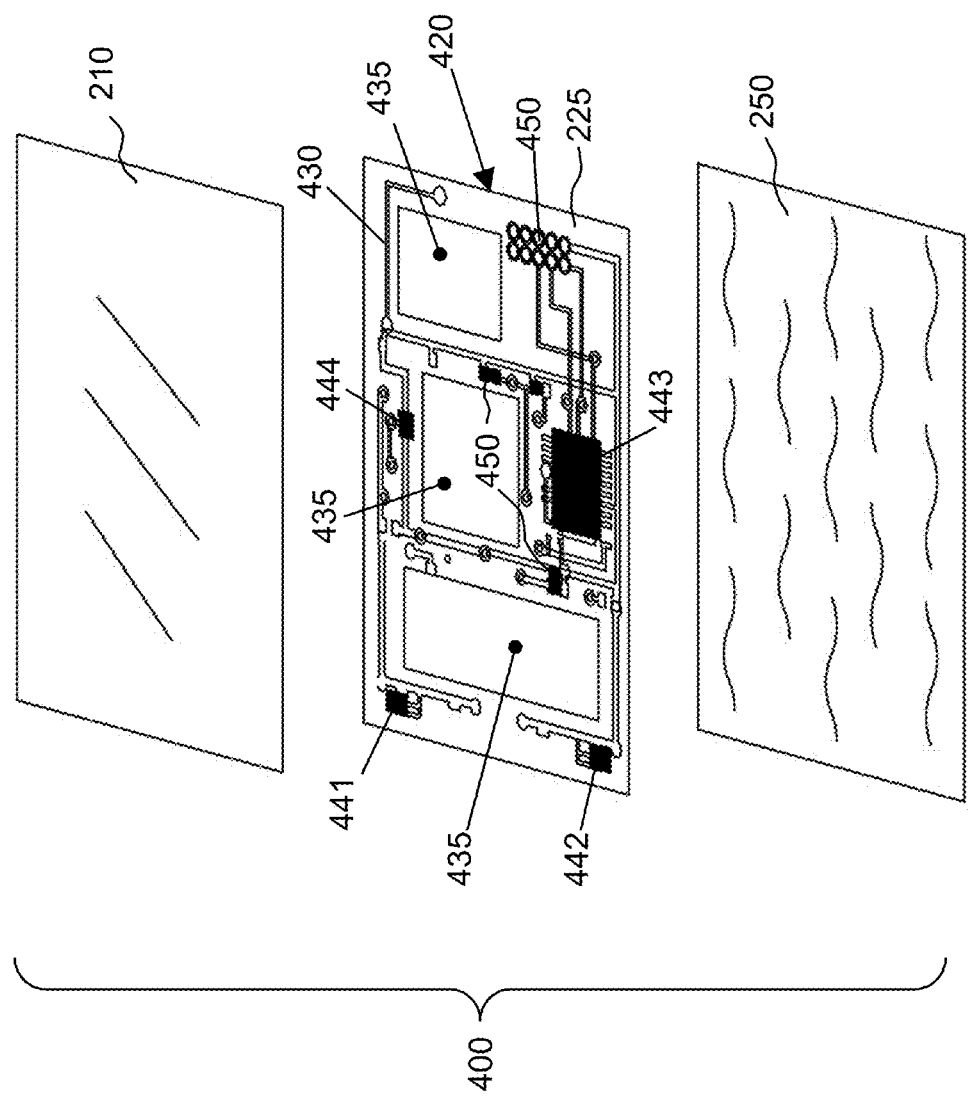
FIG. 4 is an exploded perspective view of another exemplified compliant multi-layer wearable patch in accordance with some embodiments of the present invention.

In some embodiments, referring to FIG. 4, a wearable patch 400 includes an elastic layer 210, a shearable circuit layer 420, and an adhesive layer 250. The shearable circuit layer 420 includes a support substrate 225 that includes openings 435, a conductive circuit 430, and semiconductor chips 441-444 and multiple electronic components 450 that are electrically connected to the conductive circuit 430. The semiconductor chips 441-444 can perform communications, logic, signal or data processing, control, calibration, status report, diagnostics, and other functions. The electronic components 450 can include an antenna circuit, capacitors, inductors, resistors, metal pads, diodes, transistors, amplifiers, etc. The electronic components 450 can also include sensors for measuring temperature, acceleration and movements, and chemical or biological substances. The electronic components 450 can also include electromechanical actuators, chemical injectors, etc. The elastic layer 210 is breathable to allow aspiration and moisture from the skin to be released to the environment. The openings 435 provide additional breathability to the wearable patch 400. With enough opening area on the support substrate 225, the shearable circuit layer 420 can also provide tolerate significant stress along the surface directions.

Figure 5:
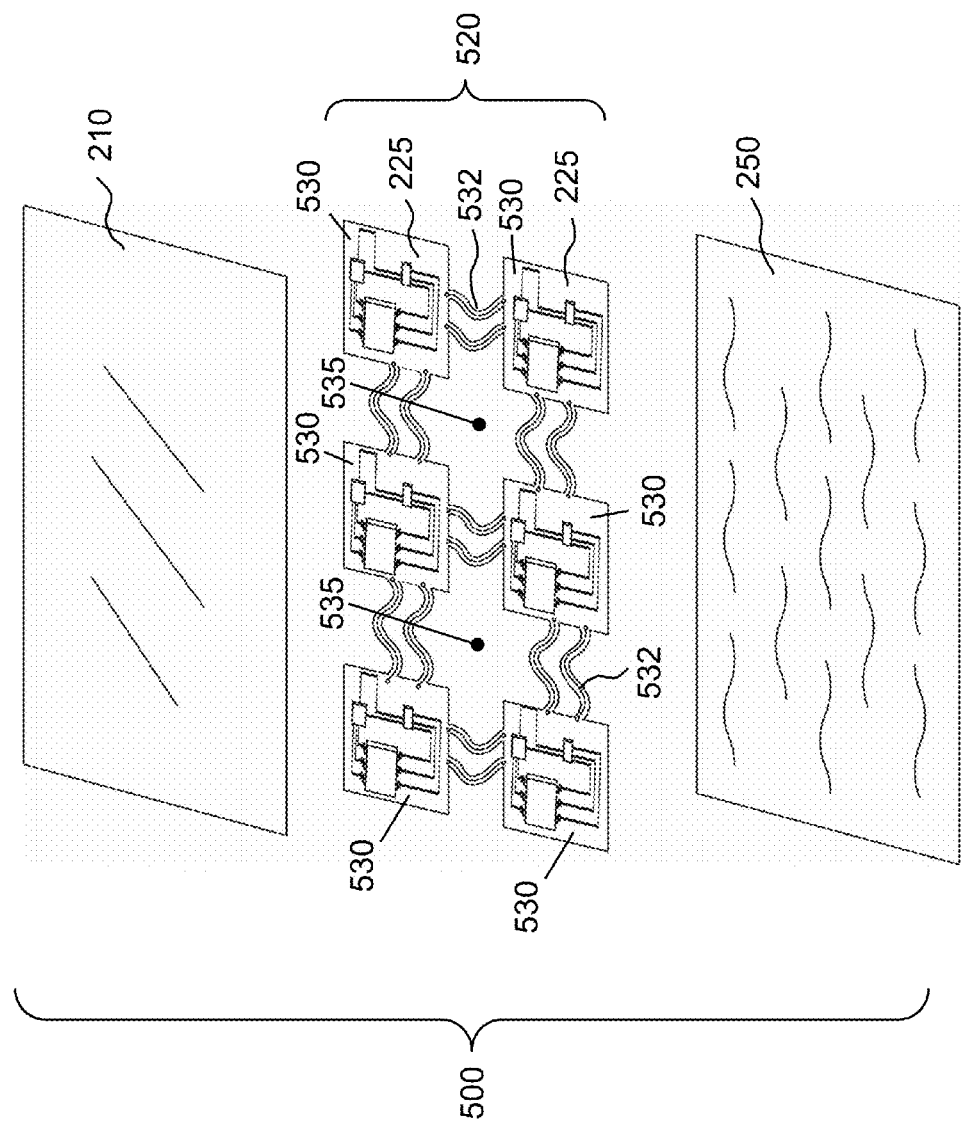
FIG. 5 is an exploded perspective view of another exemplified compliant multi-layer wearable patch in accordance with some embodiments of the present invention.

Similarly, referring to FIG. 5, a wearable patch 500 includes an elastic layer 210, a shearable circuit layer 520, and an adhesive layer 250. The shearable circuit layer 520 includes a network of circuit modules 530 connected by flexible ribbons 532 embedded with conductive lines. The support substrate 225 can be flexible (bendable) but is rigid enough to support individual IC components in the circuit modules 530. The flexible ribbon 532 can be in curly or serpentine shape, which allows stretchability when the wearable patch 500 is stretched during wearing. As described above, the elastic layers 210 is breathable to allow aspiration and moisture from the skin to be released to the environment. The network of individual IC components and/or circuit modules 530 and the flexible ribbons 532 with conductive lines define openings 535 in between to provide additional breathability to the wearable patch 500. Furthermore, opening holes or voids can be made on the circuit modules 530 to increase its breathability and the effective elasticity. The support substrate 225 can be contiguous to support the circuit modules 530 and the flexible ribbons 532 with conductive lines. In manufacturing, the support substrate 225 can be formed in a single manufacturing step from a continuous sheet of material. The openings 535 and the connection portions between the circuit modules 530 can be formed by removing material from the continuous sheet by techniques such as laser cutting and/or die cutting. It should be noted that the presently disclosed "single substrate" structure for the circuit layer is drastically different from conventional approaches, where different rigid boards/modules are connected with flexible ribbons via connectors. In our proposed approach, the modules and ribbons are made on one single continuous substrate. Openings or voids are created on the substrate to provide high effective elasticity and breathability.

Each circuit module 530 can include one or more semiconductor chips and/or electronic components on their respective portions of the support substrate 225. The semiconductor chips can perform communications, logic, signal or data processing, control, calibration, status report, diagnostics, and other functions. The electronic components can include an antenna circuit, capacitors, inductors, resistors, metal pads, diodes, transistors, amplifiers, etc. The electronic components can also include sensors for measuring temperature, acceleration and movements, and chemical or biological substances. The electronic components 450 can also include electromechanical actuators, chemical injectors, etc.

Figure 6:
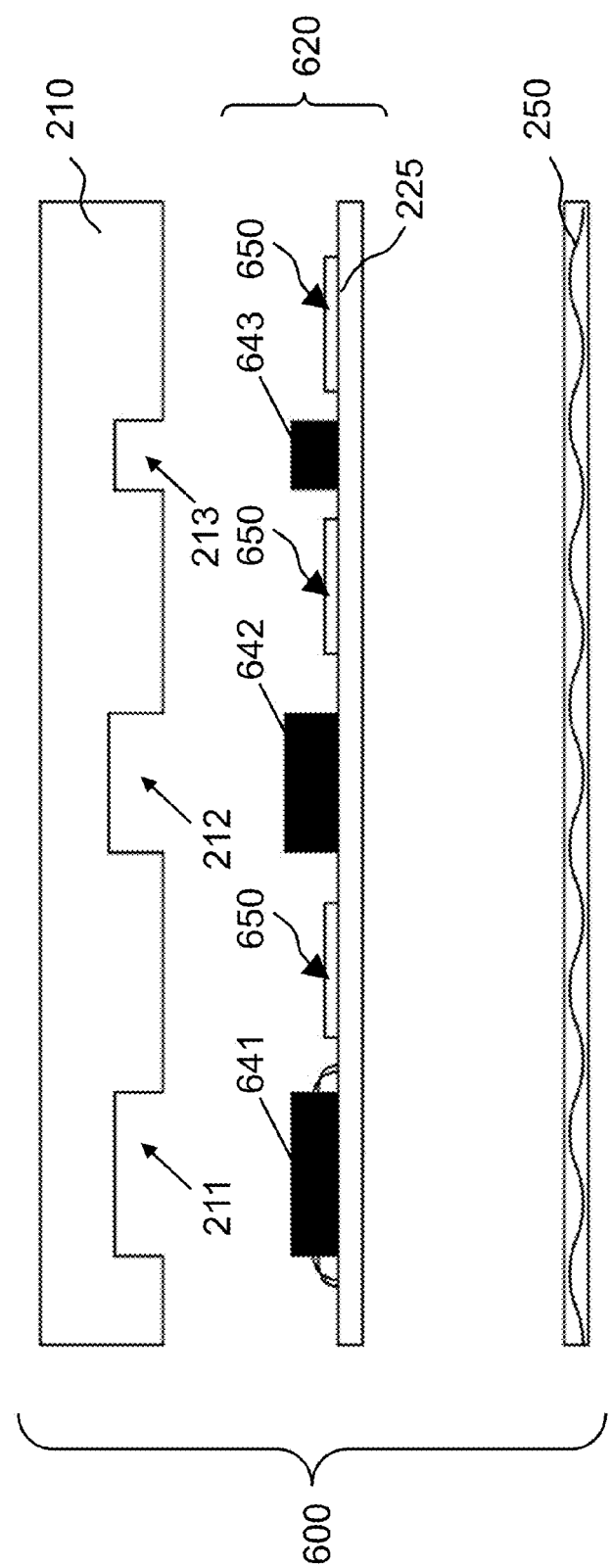
FIG. 6 is a cross-sectional view of an exemplified compliant multi-layer wearable patch in accordance with some embodiments of the present invention.

FIG. 6 is a cross-sectional view of an exemplified compliant multi-layer wearable patch 600 that includes an elastic layer 210, a shearable circuit layer 620, and an adhesive layer 250. The shearable circuit layer 620 includes a support substrate 225, a conductive circuit (not shown), and semiconductor chips 641-643 and multiple electronic components 650 that are electrically connected by a conductive circuit (not shown).

The elastic layer 210 can include recesses 211-213 that enclose the semiconductor chips 641-643, which allows the elastic layer 210 to be substantially flat upper surface. In some embodiments, the elastic layers 210 can be formed on the shearable circuit layer 620 and its associated components thereon by a fluid delivery device such as an ink jet print head, screen printing process, or flexographic process, other layer formation methods known in the art of the field. When the elastic layer 210 is formed on the shearable circuit layer 620 using a fluid delivery device, a polymeric elastic material can be deposited along the contours of the semiconductor chips 641-643 and the electronic components 650.

The semiconductor chips 641-643 can perform communications, logic, signal or data processing, control, calibration, status report, diagnostics, and other functions. The electronic components 650 can include an antenna circuit, capacitors, inductors, resistors, metal pads, diodes, transistors, amplifiers, etc. The electronic components 650 can also include sensors for measuring temperature, acceleration and movements, and chemical or biological substances. The electronic components 650 can also include electromechanical actuators, chemical injectors, etc.

Figure 7:
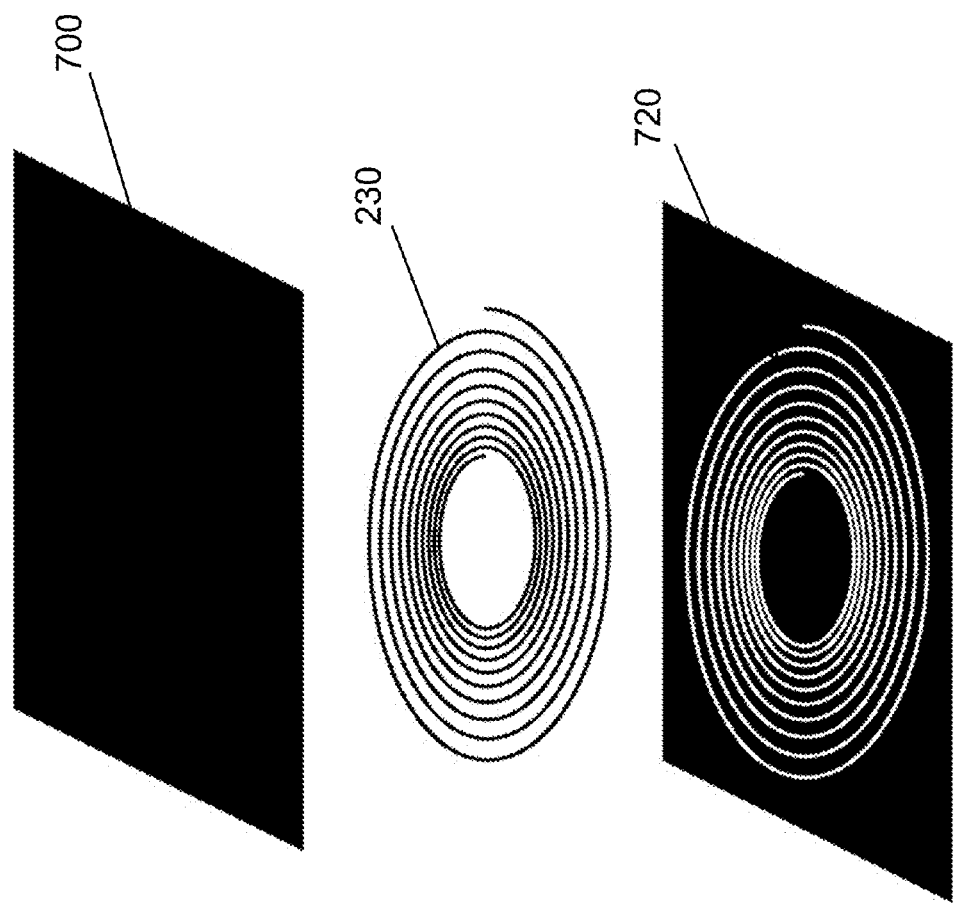
FIG. 7 illustrates the making of an exemplified shearable circuit layer in the compliant multi-layer wearable patch in accordance with some embodiments of the present invention.
Figure 8:
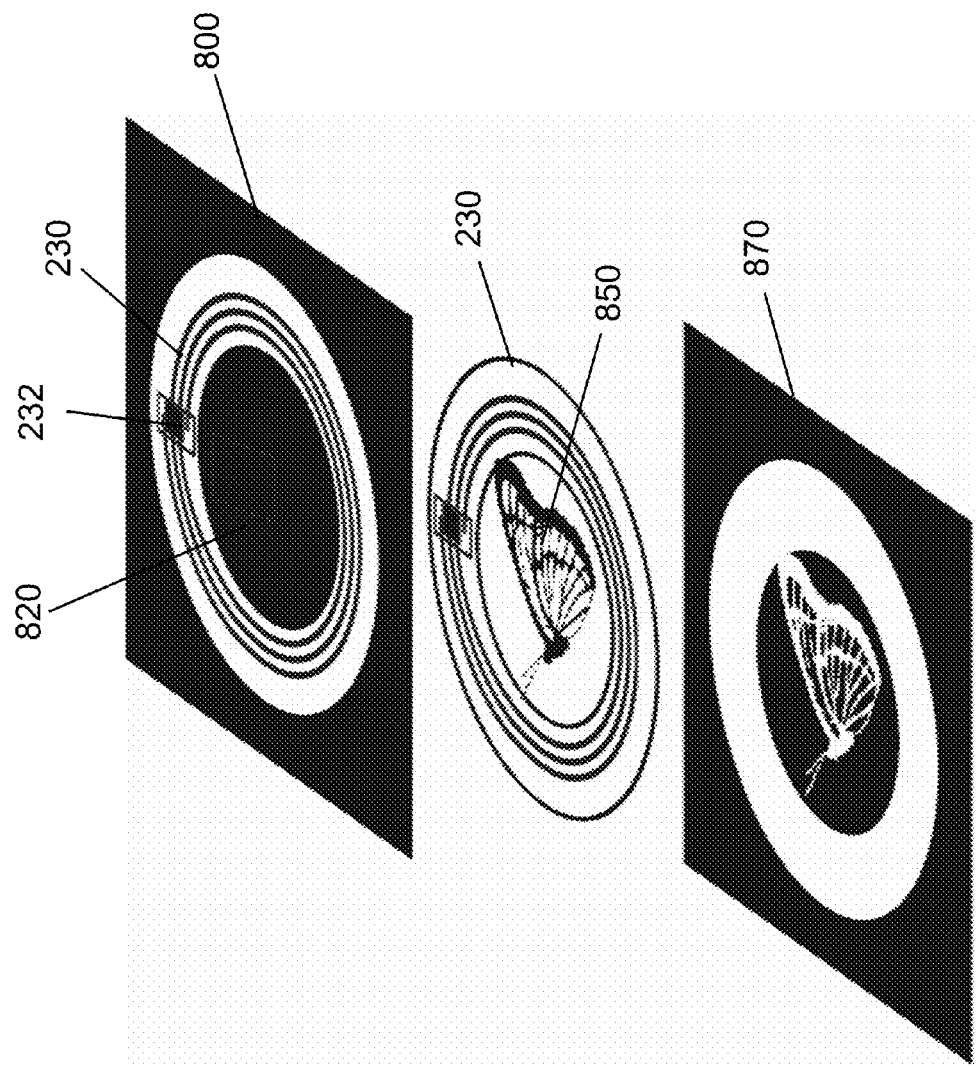
FIG. 8 illustrates the making of another exemplified shearable circuit layer in the compliant multi-layer wearable patch in accordance with some embodiments of the present invention.

FIGS. 7 and 8 illustrate exemplified processes of making shearable circuit layers in the presently disclosed compliant multi-layer wearable patches. Referring to FIG. 7, a sheet of metal material 700 is cut by a die to form an antenna circuit 230 (also shown in FIG. 2). The sheet of metal material 700 can be made of copper for example. The left over material 720 is discarded.

An aspect of the disclosed wearable patches is to provide aesthetic appeal to the users. Referring to FIG. 8, a sheet of metal material 800 is cut by a die to form an antenna circuit 230, a metal pad 232 (also shown in FIG. 2), and a central portion 820. The central portion 820 is cut again by another die to form a graphic pattern 850 made of the conductive material in the same sheet of metal material 800. The graphic pattern 850 is encircled by the antenna circuit 230. The left over material 870 is discarded.

In some embodiments, the graphic pattern 850 provides more than aesthetics to the wearable patch 200. The antenna circuit 230 can receive or transmit wireless electromagnetic signals by a LC (inductor-capacitor) circuit. When the graphic pattern 850 is made using a conductive material (such as the same metal layer from which the antenna circuits 230 is formed), the graphic pattern 850 can modify the inductance-capacitance response by producing a counter inductive eddy current in the graphic pattern 850, which can increase the stability of wireless reception and transmission, and broaden the frequency response window of the wearable patch.

It should be noted that the disclosed wearable patches are also compatible with two or more layers of conductive circuits (including antenna and other logic circuits) and each dielectric layer in between them, which can result in additional improved communication quality or further increased transmission data rate. More details about wearable patches having multiple shearable circuit layers are disclosed in commonly assigned pending U.S. patent application Ser. No. 14/454,457, titled "Stretchable multi-layer wearable tag capable of wireless communications", the disclosure of which is incorporated herein by reference.

Figure 9:
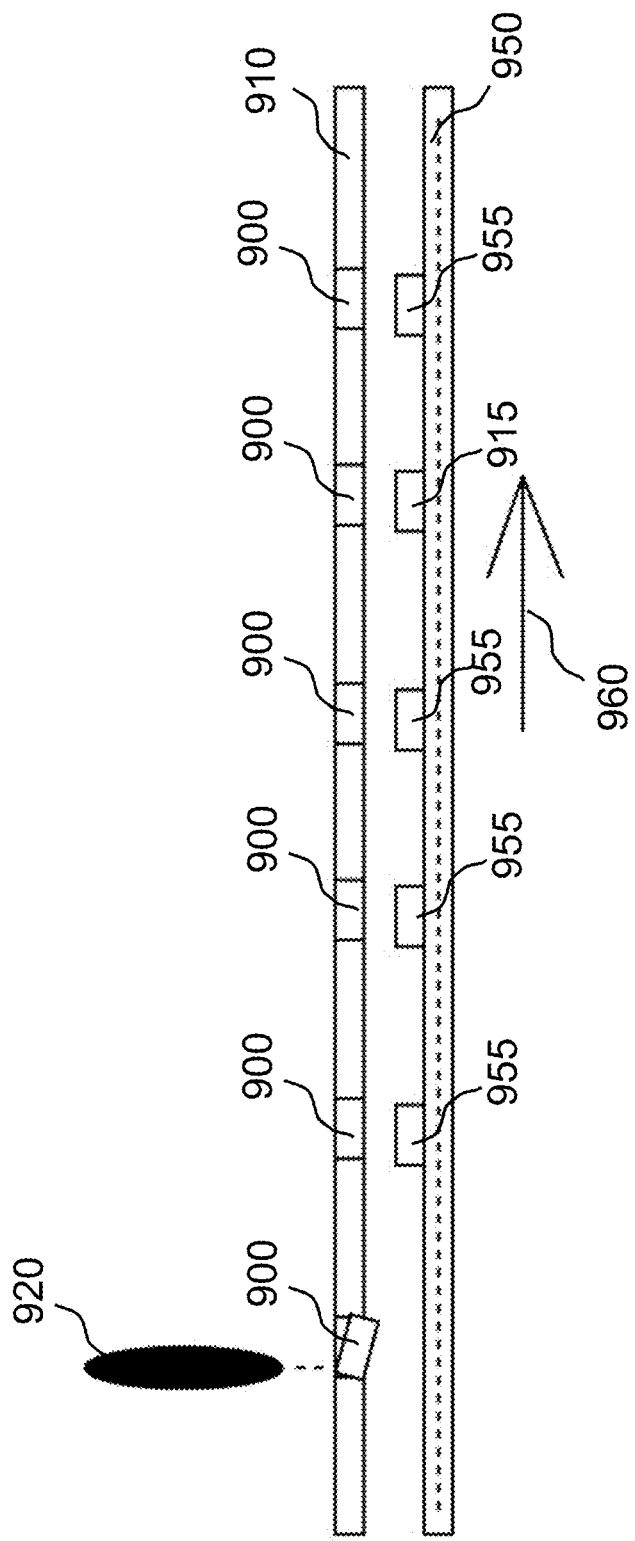
FIG. 9 illustrates a manufacturing and packaging process in which compliant multi-layer wearable patches are attached to a substrate in a roll-to-roll process in accordance with some embodiments of the present invention.

FIG. 9 illustrates a manufacturing and packaging process in which a plurality of compliant multi-layer wearable patches 900 are formed in a substrate 910, as described above. The compliant multi-layer wearable patches 900 are cut off from the substrate 910 by a laser device 920 using laser cutting technique. The compliant multi-layer wearable patches 900 are transferred and attached to a continuous substrate 950 to form separate compliant multi-layer wearable patches 955. The upper surface of the continuous substrate 950 or the lower surface of the substrate 910 is pre-coated with an adhesive layer to allow the compliant multi-layer wearable patches 900. The continuous substrate 950 can be a web transported in a direction 960 and can be rolled up by a take-up roller (not shown). The continuous process and roll-up format make it convenient to package, store, and distribute compliant multi-layer wearable patches 955 to the users in the field. To use a compliant multi-layer wearable patch 955, it can be peeled it off from the continuous substrate 950 with the adhesive attached, and pressed the surface with the adhesive against to the skin of a user.

Figure 10:
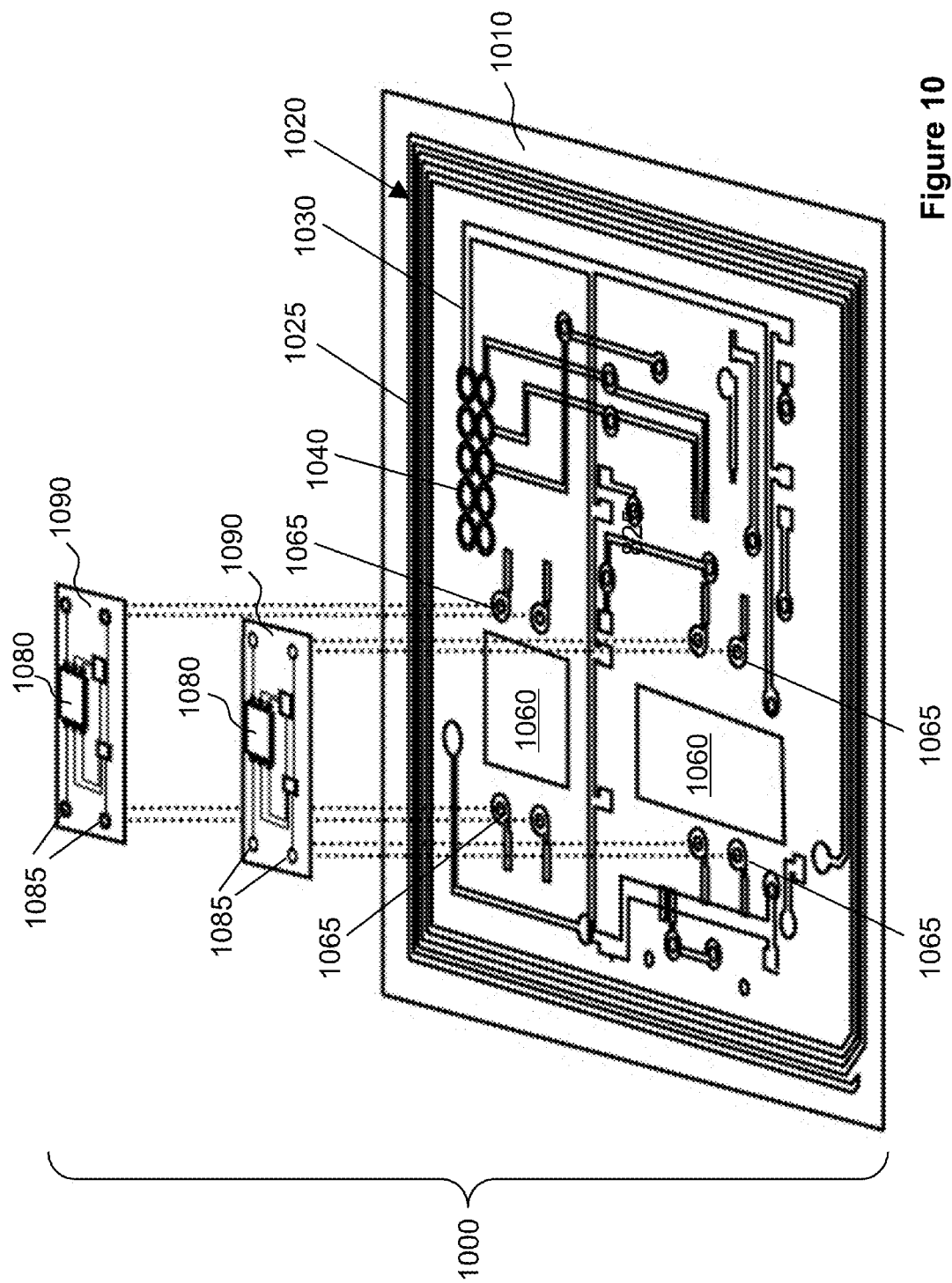
FIG. 10 is an exploded perspective view of a shearable circuit layer having stress relief structures around semiconductor chips, wherein the shearable circuit layer is compatible with the compliant multi-layer wearable patches in accordance with some embodiments of the present invention.

The presently disclosed wearable patch can further relieve stresses during usage by incorporating a multi-layer circuit structure in the wearable patch. Referring to FIG. 10, a multi-layer circuit structure 1000, which is compatible with the shearable circuit layers in the above disclosed wearable patches (FIGS. 1-9), includes a support substrate layer 1010 and a conductive circuit 1020 that can include an antenna circuit 1025, an auxiliary circuit 1030, electronic components 1040, and metal pads 1065. The electronic components can include an antenna circuit, capacitors, inductors, resistors, metal pads, diodes, transistors, amplifiers, etc. The electronic components 1040 can include sensors for measuring temperature, acceleration and movements, and chemical or biological substances. The electronic components 1040 can also include electromechanical actuators, chemical injectors, etc.

The support substrate layer 1010 include strategically positioned one or more openings 1060 to make multi-layer circuit structure 1000 shearable and stretchable under external stresses.

The multi-layer circuit structure 1000 also includes one or more compliant strap layers 1090 disposed across the one or more openings 1060, and one or more semiconductor chips 1080 on one or more compliant strap layers 1090. Each strap layer 1090 includes a compliant non-conductive substrate and connection points 1085 that are electrically connected to the respective semiconductor chips 1080. The strap layer 1090 can also include a logic circuit in connection with the one or more semiconductor chips 1080, logic circuit including electronic components such as a capacitor, a resistor, a diode, or an inductor. When the multi-layer circuit structure 1000 is assembled, the connection points 1085 are soldered to the metal pads 1065 to connect the semiconductor chips 1080 to the conductive circuit 1020. The compliant strap layers 1090 can be made of compliant and breathable materials such as elastomers, viscoelastic polymers, such as silicone, and medical grade polyurethane. The support substrate layer 1010 includes openings 1065 under the compliant strap layers 1090.

One advantage of the multi-layer circuit structure is that it can effectively distribute and relieve stresses experienced by wearable patches and the shearable circuit layer. Normally the stress is the highest around rigid semiconductor chips in wearable patches. The separate compliant strap layers 1090 and the soldering points as well as the openings 1065 together provide more slacks for the support substrate layer 1010 and the compliant strap layers 1090 to adapt to strains, which minimizes stresses in the disclosed wearable patches.

Figure 11:
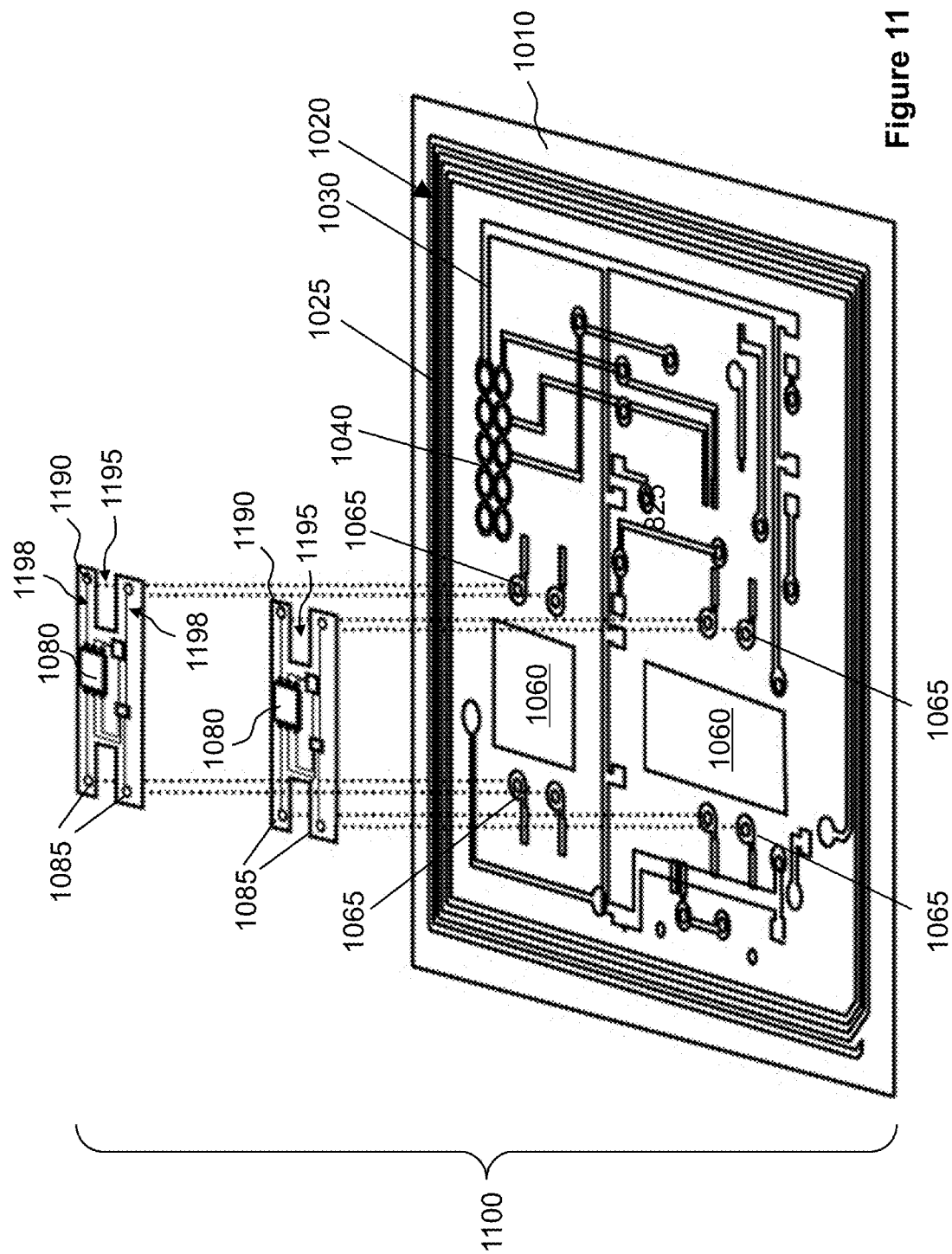
FIG. 11 is an exploded perspective view of another shearable circuit layer having stress relief structures around semiconductor chips, wherein the shearable circuit layer is compatible with the compliant multi-layer wearable patches in accordance with some embodiments of the present invention.

In some embodiments, referring to FIG. 11, a multi-layer circuit structure 1100 includes compliant strap layers 1190 that includes narrow stripes 1098 separated by cuts 1195 in between. The connection points 1085 are formed at the ends of the narrow strips 1098. The narrow stripes 1098 are. The narrow stripes 1098 provide more elasticity and compliance, which reduces the stresses experienced by the center portions of the compliant strap layers 1190 around the semiconductor chips 1080, in response to elongations of the multi-layer circuit structure 1100.

Figure 12:
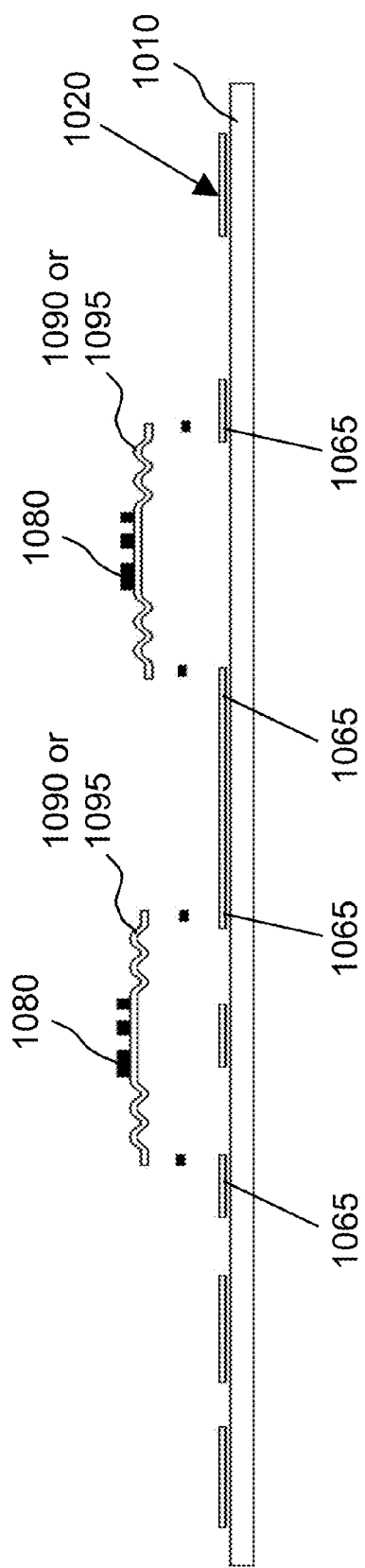
FIG. 12 is a cross-sectional view of a shearable circuit layer having stress relief structures around semiconductor chips, as illustrated in FIGS. 10 and 11.
Figure 13:
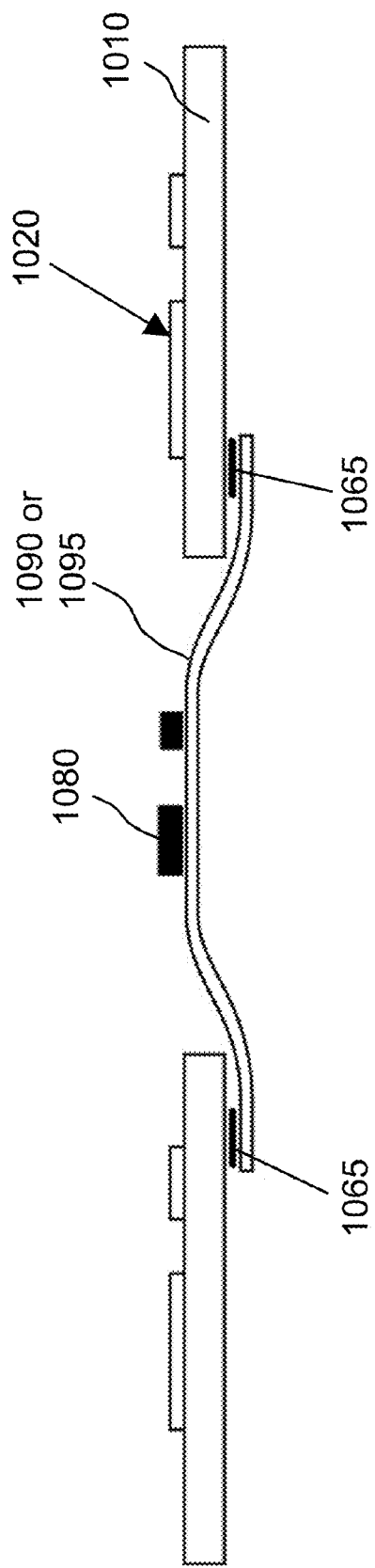
FIG. 13 is a cross-sectional view of a portion of a shearable circuit layer having stress relief structures around semiconductor chips, wherein the shearable circuit layer is compatible with the compliant multi-layer wearable patches in accordance with some embodiments of the present invention.

The above described compliant strap layers 1090 or 1190 can be connected (e.g. by ultrasonic or welding soldering) to the metal pads 1065 located either above (FIG. 12) or below (FIG. 13) the substrate compliant layer 1010. Moreover, as shown in FIG. 13, the compliant strap layers 1090 or 1190 can be compressed to a buckled shape prior to connecting the connection points to the metal pads 1065. In other words, extra slacks are built in the strap layers 1090 or 1190, which allow more room for the compliant strap layers 1090 or 1190 to stretch in response to elongation distortions in the wearable patches during usage.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the usages of the disclosed wearable patches are not limited by the examples given above; they can be applicable to many other fields. The materials suitable for the different layers of the wearable patches are also not limited by the examples provided. The layouts and forms of the elastic layer, the compliant strap layers, the breathing openings, the decorative pattern, the semiconductor chip, the antenna, the metal pads, and the connection leads can have other configurations without deviating from the present invention.

What is claimed is:

1. A method for making a stretchable wireless device, comprising:
    obtaining a continuous sheet of a polymeric material that comprise polyimide, polyester, aramid, glass epoxy, or polyethylene naphalate, wherein the continuous sheet of the polymeric material comprises portions respectively for formations of flexible ribbons and a plurality of support substrates;
    removing materials from the continuous sheet of the polymeric material in a single manufacturing step to form the plurality of support substrates and flexible ribbons;
    embedding first conductive circuits in the plurality of support substrates;
    mounting one or more semiconductor chips in connection with the first conductive circuit to form a plurality of circuit modules each associated with one of the plurality of substrates;
    embedding second conductive circuits in the flexible ribbons, the second circuits connected with at least two of the first conductive circuits to form a network of circuit modules, wherein the plurality of circuit modules and the second circuits are configured to wirelessly communicate with an external device, wherein the plurality of circuit modules and the flexible ribbons embedded with the second conductive circuits form a support substrate structure;
    forming an adhesive layer below the support substrate structure; and
    forming an elastic layer on the support substrate.

2. The method of claim 1, wherein the step of removing materials from the continuous sheet of the polymeric material comprises:
    cutting the continuous sheet of material with a die or with a laser.

3. The method of claim 1, wherein the step of removing materials from the continuous sheet of the polymeric material comprises:
    forming one or more openings in the flexible ribbons and the plurality of circuit modules to allow the shearable circuit layer to be stretchable and breathable.

4. The method of claim 1, wherein the flexible ribbons have curly or serpentine shapes.

5. The method of claim 1, wherein the plurality of support substrates have a Young's Modulus higher than 0.5 Gpa, wherein the elastic layer has a Young's Modulus lower than 0.3 Gpa.

* * * * *